United States Patent
Shi et al.

(10) Patent No.: US 11,761,003 B2
(45) Date of Patent: Sep. 19, 2023

(54) ADENO-ASSOCIATED VIRUS FOR ACTIVATING RNA-NEAT1 OVER-EXPRESSION AND APPLICATIONS THEREOF

(71) Applicant: Eye Institute of Shandong First Medical University, Shandong (CN)

(72) Inventors: Weiyun Shi, Shandong (CN); Qun Wang, Shandong (CN); Qingjun Zhou, Shandong (CN); Shengqian Dou, Shandong (CN); Hui Jiang, Shandong (CN); Bin Zhang, Shandong (CN)

(73) Assignee: Eye Institute of Shandong First Medical University, Shandong (CN)

( * ) Notice: Subject to any disclaimer, the term of this patent is extended or adjusted under 35 U.S.C. 154(b) by 0 days.

(21) Appl. No.: 18/045,127

(22) Filed: Oct. 7, 2022

(65) Prior Publication Data

US 2023/0085277 A1 Mar. 16, 2023

Related U.S. Application Data

(63) Continuation of application No. PCT/CN2022/095885, filed on May 30, 2022.

(30) Foreign Application Priority Data

Jun. 2, 2021 (CN) .......................... 202110612589.0

(51) Int. Cl.
| | | |
|---|---|---|
| C07H 21/04 | (2006.01) | |
| C12N 15/113 | (2010.01) | |
| A61P 27/02 | (2006.01) | |
| A61K 9/00 | (2006.01) | |
| C12N 15/86 | (2006.01) | |

(52) U.S. Cl.
CPC .......... *C12N 15/113* (2013.01); *A61K 9/0048* (2013.01); *A61P 27/02* (2018.01); *C12N 15/86* (2013.01); *C12N 2310/14* (2013.01); *C12N 2750/14143* (2013.01)

(58) Field of Classification Search
None
See application file for complete search history.

(56) References Cited

U.S. PATENT DOCUMENTS

2020/0158716 A1    5/2020   Shalek et al.

FOREIGN PATENT DOCUMENTS

CN            113350367 A        9/2021

OTHER PUBLICATIONS

Bai, Yan-Hui et al.; "LncRNA NEAT1 promotes inflammatory response and induces corneal neovascularization"; Journal of Molecular Endocrinology; vol. 4, No. 61; Oct. 15, 2018; pp. 1-29.
Zheng, Jiusheng et al.; "Research progress of long non-coding RNA in eye diseases"; International Eye Science; vol. 10, No. 20; Oct. 31, 2020; pp. 1740-1743.
Yan, Yanyun et al.; "Fuchs' endothelial corneal dystrophy"; Journal of Clinical Ophthalmology; vol. 25, No. 2; Apr. 30, 2017; pp. 177-182.

*Primary Examiner* — Kimberly Chong
(74) *Attorney, Agent, or Firm* — NKL Law; Allen Xue

(57) ABSTRACT

Long-chain non-coding RNA NEAT1 are used in the preparation of drugs for the treatment of Fuchs' endothelial corneal dystrophy. Overexpression of the long-chain non-coding RNA NEAT1 can effectively reduce corneal endothelial damage, alleviate the symptoms of corneal edema, can be used for the treatment of Fuchs' endothelial corneal malnutrition.

13 Claims, 3 Drawing Sheets

Specification includes a Sequence Listing.

ADENO-ASSOCIATED VIRUS FOR ACTIVATING RNA-NEAT1 OVER-EXPRESSION AND APPLICATIONS THEREOF

CROSS-REFERENCE TO RELATED APPLICATIONS

This application is a continuation of PCT International Application No. PCT/CN2022/095885, filed on May 30, 2022, which claims the benefit of priority to Chinese Application No. 202110612589.0, filed on Jun. 2, 2021, the content of each is incorporated herein by reference in its entirety.

INCORPORATION OF SEQUENCE LISTING

This application contains a sequence listing submitted in Computer Readable Form (CRF). The CFR file containing the sequence listing entitled "PA741-0002-Sequence-Listing.xml", which was created on Oct. 7, 2022, and is 2,401 bytes in size. The information in the sequence listing is incorporated herein by reference in its entirety.

TECHNICAL FIELD

The present invention belongs to the field of medical technology, specifically relates to the application of long-chain non-coding RNA NEAT1 and overexpressed RNA NEAT1 sgRNA and adeno-associated viruses and applications.

BACKGROUND

Fuchs' endothelial corneal dystrophy (FECD), also known as cornea guttata, is a common hereditary corneal endothelial degeneration characterized by the development of corneal stromal and epithelial edema, resulting in significant loss of vision. Currently, the clinical treatment option for the treatment of Fuchs' endothelial corneal dystrophy is to undergo a corneal transplant. Although corneal transplant surgery has largely succeeded in treating Fuchs' endothelial corneal dystrophy, there are still shortcomings such as invasiveness, insufficient number of corneal donors, and high price, prompting the development of other therapeutic treatments.

SUMMARY OF THE INVENTION

To solve the above problems, the present invention provides applications of a long-chain non-coding RNA-NEAT1 and a sgRNA for RNA-NEAT1 over-expression and an adeno-associated viruses and the applications thereof. The invention performs over-expression of long-chain non-coding RNA-NEAT1 in anterior chamber to treat Fuchs' endothelial corneal dystrophy, which can effectively reduce corneal endothelial damage and relieve symptoms of corneal edema.

In order to achieve the above purposes, the present invention provides the following technical solutions: The present invention provides an application of a long-chain non-coding RNA NEAT1 in the preparation of drugs for treating Fuchs' endothelial corneal dystrophy.

The present invention provides a sgRNA for long-chain non-coding RNA-NEAT1 over-expression, the nucleotide sequence of said sgRNA is shown as SEQ ID NO: 1.

The present invention provides an adeno-associated virus AAV9-Neat1-sgRNA for long-chain non-coding RNA-NEAT1 over-expression, said adeno-associated virus AAV9-Neat1-sgRNA comprising said sgRNA described in the above technical solutions.

Optionally, the skeleton vector of said adeno-associated virus AAV9-Neat1-sgRNA comprises GV639.

Optionally, the titer of the packaging of said adeno-associated virus AAV9-Neat1-sgRNA is $2 \times 10^{12}$ to $3 \times 10^{12}$ v.g./mL.

The present invention provides a method of treating Fuchs' endothelial corneal dystrophy, wherein said adeno-associated virus AAV9-Neat1-sgRNA described in the above technical solutions is used.

Optionally, said adeno-related virus AAV9-Neat1-sgRNA is performed into anterior chamber by means of injection for treatment; the injection dose of said adeno-associated virus AAV9-Neat1-sgRNA is preferably 0.5 to 2 µL.

The present invention provides an application of said sgRNA described in the above technical solutions or said adeno-associated virus AAV9-Neat1-sgRNA described in the above technical solutions in preparing drugs for treating Fuchs' endothelial corneal dystrophy.

The present invention provides an application of said long-chain non-coding RNA-NEAT1 or said sgRNA described in the above technical solutions or said adeno-associated virus AAV9-Neat1-sgRNA described in the above technical solutions in preparing drugs for relieving symptoms of corneal edema.

The present invention provides an application of said long-chain non-coding RNA-NEAT1 or said sgRNA described in the above technical solutions or said adeno-associated virus AAV9-Neat1-sgRNA described in the above technical solutions in preparing drugs for relieving oxidative damage of corneal endothelium.

Beneficial Effects

The present invention provides an application of a long-chain non-coding RNA-NEAT1 in the preparing drugs for treating Fuchs' endothelial corneal dystrophy. Long-chain non-coding RNA-NEAT1 overexpression can effectively reduce corneal endothelial damage and alleviate symptoms of corneal edema, which can be used for the treatment of Fuchs' endothelial corneal dystrophy, and greatly simplifies the procedures and risks of treatment, without the need for corneal transplantation, with sufficient sources and low treatment costs.

DETAILED DESCRIPTION OF THE EMBODIMENTS

The present invention provides a sgRNA for long-chain non-coding RNA-NEAT1 over-expression, the nucleotide sequence of said sgRNA is as shown in SEQ ID NO: 1, the specific nucleotide sequence is aaggatcattgagcaatctga. In the present invention, said long-chain non-coding RNA-NEAT1 is obtained according to NEAT1 design. Said sgRNA for long-chain non-coding RNA-NEAT1 overexpression provided in present invention could construct an adeno-associated viral vector which has the overexpressed long-chain non-coding RNA-NEAT1, and could be injected into anterior chamber of the eye by means of anterior chamber injection. Then long-chain non-coding RNA-NEAT1 overexpression is performed in the anterior chamber, and Fuchs' endothelial corneal dystrophy is treated.

Figure 1:
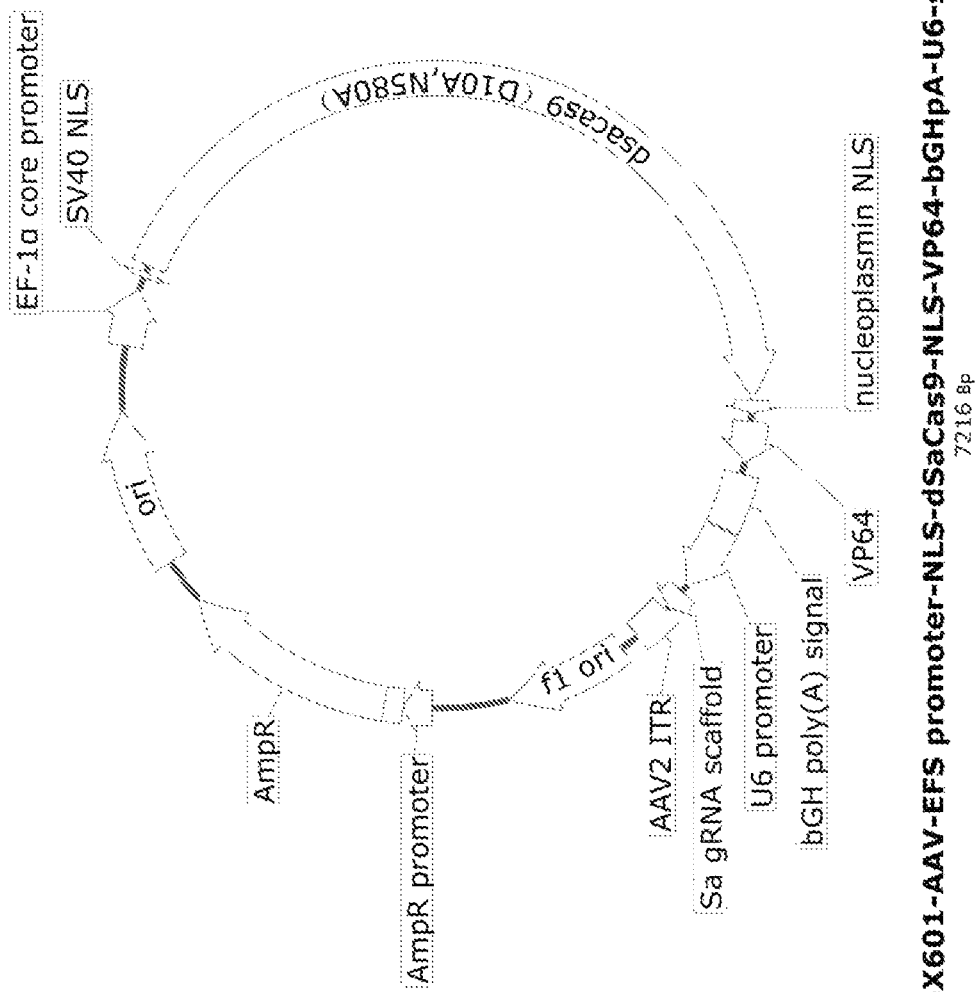
FIG. 1 is a structure diagram of an adeno-associated virus AAV9-Neat1-sgRNA.

The present invention provides an adeno-associated virus AAV9-Neat1-sgRNA for long-chain non-coding RNA-NEAT1 over-expression, said adeno-associated virus AAV9-Neat1-sgRNA comprising said sgRNA described in the above technical scheme. The present invention takes the adenovirus as a skeleton vector, said sgRNA described in the above technical scheme is inserted into the skeleton vector. In the present invention, the skeleton vector of said adeno-associated virus AAV9-Neat1-sgRNA preferably comprises GV639. The present invention has no special requirements for the method of inserting sgRNA, conventional technical means in the art may be used. The present invention preferably utilizes the dSaCas9 system to synthesize said adeno-associated virus AAV9-Neat1-sgRNA, the structure of the synthesized adeno-associated virus AAV9-Neat1-sgRNA is shown in FIG. 1. In the present invention, the final packaging titer of the synthesized adeno-associated virus AAV9-Neat1-sgRNA is preferably $2\times10^{12}$ to $3\times10^{12}$ v.g./mL, further preferably $3\times10^{12}$ v.g./mL. The present invention comprises: inserting said sgRNA described in the above technical scheme into an adenoviral vector to obtain an adeno-associated virus AAV9-Neat1-sgRNA which could be used to over-express long-chain non-coding RNA-NEAT1, injecting said adeno-associated virus AAV9-Neat1-sgRNA provided by the present invention into the anterior chamber of the eye by means of anterior chamber injection, performing the long-chain non-coding RNA-NEAT1 overexpression in the anterior chamber, so as to reach the purpose of treating Fuchs' endothelial corneal dystrophy. The present invention has no special requirements for the means of anterior chamber injection in the embodiments, those well known by the skilled person in the art may be applied.

The present invention provides an application of said sgRNA in the technical solution or said adeno-associated virus AAV9-Neat1-sgRNA in the technical solution in preparing drugs for treating Fuchs' endothelial corneal dystrophy.

The present invention provides an application of a long-chain non-coding RNA NEAT1 or said sgRNA in the technical solution or said adeno-associated virus AAV9-Neat1-sgRNA in the technical solution in preparing drugs for relieving symptoms of corneal edema.

The present invention provides an application of a long-chain non-coding RNA NEAT1 or said sgRNA in the technical solution or said adeno-associated virus AAV9-Neat1-sgRNA in the technical solution in preparing drugs for relieving oxidative damage of corneal endothelium.

The present invention provides a method for treating Fuchs' endothelial corneal dystrophy, by using said adeno-associated virus AAV9-Neat1-sgRNA disclosed in the above technical solution for treatment. Said adeno-associated virus AAV9-Neat1-sgRNA provided by the invention is preferably injected into the anterior chamber for treatment through injection; the injection dosage of said adeno-associated virus AAV9-Neat1-sgRNA is preferably 0.5 to 2 µL, further preferably 1 µL. The method for treating Fuchs' corneal endothelial dystrophy provided by the present invention requires only one dose of injection, which greatly simplifies the operation and lowers the risk of treatment, and does not need corneal transplantation; the source is sufficient; the treatment cost is low; the effect of treating Fuchs' endothelial corneal dystrophy is good and it can effectively reduce corneal endothelial injury and relieve corneal edema.

To further illustrate the present invention, the following embodiments are provided to describe the applications of the long-chain non-coding RNA-NEAT1, the sgRNA for RNA-NEAT1 overexpression, the adeno-associated virus and their applications thereof in detail, but they should not be understood as limiting the scope of protection of the present invention.

Example 1

Construction of Adeno-Associated Virus AAV9-Neat1-sgRNA

The invention uses long-chain non-coding RNA-NEAT1 to design sgRNA, wherein the long-chain non-coding RNA-NEAT1 ID is 66961; the nucleotide sequence of sgRNA is shown as SEQ ID NO: 1. Connecting the sgRNA to the GV639 adenovirus vector, sequencing the ligated product after TOP10 competent transformation and positive result from colony PCR, then the adeno-associated virus AAV9-Neat1-sgRNA with the correct sequence of sgRNA expression was obtained. The sgRNA was synthesized by GK Gene Chemical Technology Co., Ltd.; GV639 adenovirus vector and TOP10 competent cell was purchased from GKA GEN CHEMICAL TECHNOLOGY CO., LTD.; The colony PCR primer was purchased from Shanghai Jierui Biological Engineering Co., Ltd. The resulting packaged adeno-associated virus AAV9-Neat1-sgRNA has a titer of $2.18\times10^{12}$ v.g./mL.

Example 2

Investigation into the Treatment of Fuchs' Endothelial Corneal Dystrophy select 8 to 12 weeks old C57BL/6.1 female mice (weight of about 20 g) to construct Fuchs' endothelial corneal dystrophy model, and then investigate the therapeutic effect of Fuchs' endothelial corneal dystrophy treatment. The method of model construction refers to the following literature: Liu et al., Ultraviolet A light induces DNA damage and estrogen-DNA adducts in Fuchs endothelial corneal dystrophy causing females to be more affected. PNAS Latest Articles, Jan. 7, 2020 117(1)5 73-583.

In the test, the C57BL/6J female mice are randomly divided into three groups, which respectively is Neat1 over-expression group, NAC (N-acetyl-L-cysteine) group and control group.

Neat1 over-expression group: 4 weeks before model construction, inject the adeno-associated virus AAV9-Neat1-sgRNA of Example 1 into the anterior chamber of the mice; the amount of injection for a single eye is 1 µL, and one injection is performed, so that long-chain non-coding RNA-Neat1 is overexpressed in the anterior chamber; During model construction. C57BL/6J female mice are placed in a climate-controlled animal facility and kept under cyclic UVA irradiation for 12 h.

NAC group: 2 days before the UVA irradiation. C57BL/6J female mice are fed with NAC-containing water, the daily intake NAC is 1 g/kg, and the NAC-containing water feeding lasts for 3 months.

Control group (NC): 4 weeks before model construction, inject a control virus into the anterior chamber of the mice; the preparation method of the control virus is the same as that of the adeno-associated virus AAV9-Neat1-sgRNA in Example 1, while the difference is that the nucleotide sequence of the sgRNA in Example 1 is replaced by SEQ ID NO: 3, and its specific nucleotide sequence is CACCGGA-GACCACGGCAGGTCTCA. Injection dosage, injection method and model construction are the same as those of Neat1 over-expression group.

Track the thickness of the central cornea of mice by OCT, and after the treatment, intraperitoneally inject ketamine (100 mg/kg) and toluazide (20 mg/kg) into mice to anesthetize the mice, and then perform ZOI and DAPI staining. ZOI reagent was purchased from Invitrogen and DAPI reagent was purchased from Solebao. The test results are shown in FIGS. 2-4.

Figure 2:
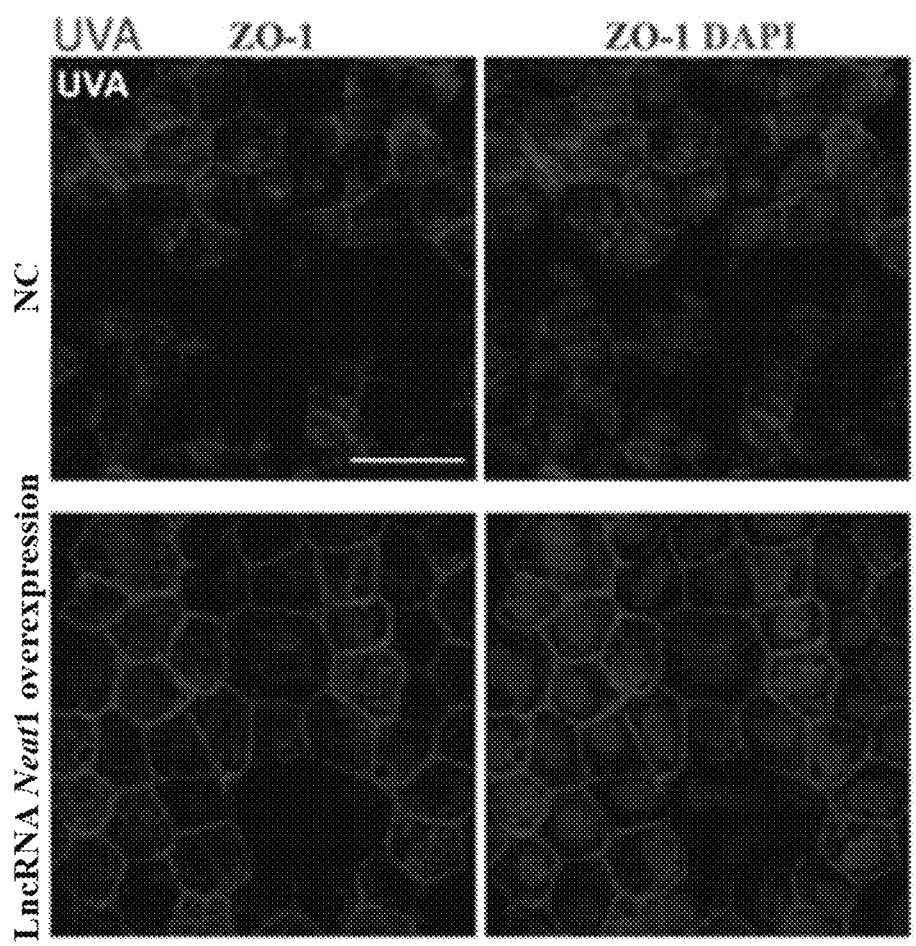
FIG. 2 shows the ZOI and DAPI fluorescent staining results of mouse corneal endothelium from different treatment groups.
Figure 3:
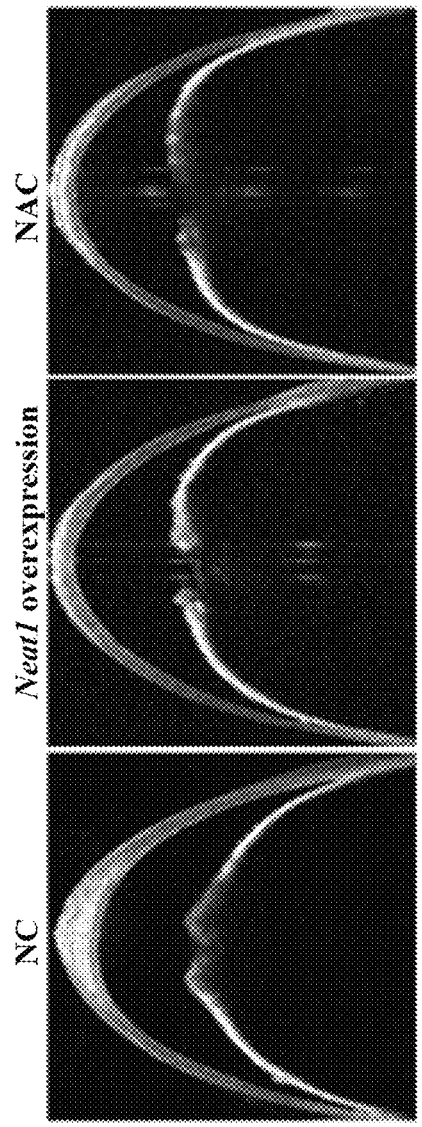
FIG. 3 shows the effects of different treatment on the thickness of the mouse central cornea.

FIG. 2 shows the ZOI and DAPI fluorescent staining results of mouse corneal endothelium from different treatment groups. From the results shown in FIG. 2, it can be seen that the FECD mouse corneal endothelium in the Neat1 over-expression group maintains a better morphology than those in the control group.

NAC (N-acetyl-L-cysteine) is commonly used as an antioxidant; in previous studies, it can be used for relieving UVA-induced FECD symptoms by making the mice ingesting NAC in the manner of continuously feeding water. To evaluate the effect of Neat1 over-expression on mouse corneal endothelial FECD symptoms, the invention adds NAC group mice as active control. FIG. 3 shows the effects of different treatment on the thickness of the mouse central cornea; From the results shown in FIG. 3, it can be seen that the central cornea thickness in Neat1 over-expression group is significantly lower than that in NC group, and close to the cornea thickness in NAC group.

Figure 4:
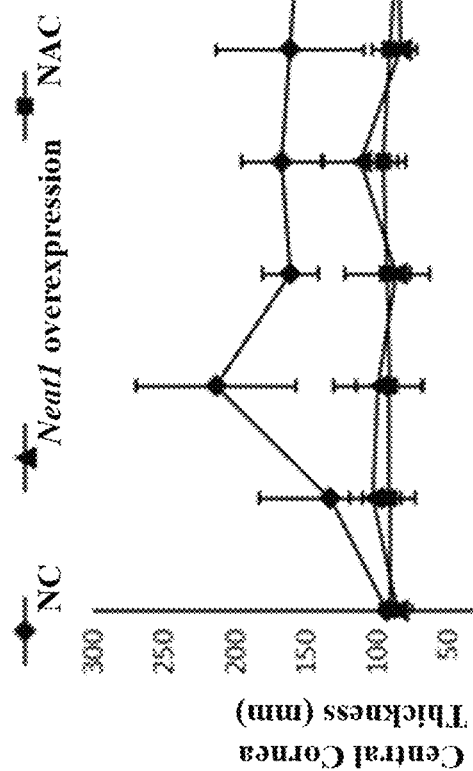
FIG. 4 shows the change of mouse central cornea thickness over time in different treatment groups.

FIG. 4 shows the change of central cornea thickness over time in mice from different treatment groups. From the results shown in FIG. 4, it can be seen that the mouse corneal endothelial thickness in Neat1 over-expression group at all time points are significantly lower than that in NC group, and very close to the NAC group, which effectively alleviated the symptoms of corneal edema in FECD mice.

The above results suggest that the Neat1 group can effectively relieve the corneal endothelial injury symptom of FECD mouse; combining with the result from the above-mentioned mouse corneal endothelial oxidative damage test and comparison with the antioxidant NAC group mouse, it further suggest that Neat1 is likely to achieve the regulation of corneal endothelial redox homeostasis and FECD pathogenesis by regulating oxidative stress response, and reveals the important biological function and clinical application potential of Neat1 in the corneal endothelium.

Although the above embodiments make a detailed description of the present invention, but it is only a part of examples of the present invention, not all embodiments. Any other embodiments made by the skilled in the art based on the technical content disclosed in present embodiments without creative activities, fall within the protection scope of the present invention.

The invention claimed is:

1. A sgRNA for long-chain non-coding RNA-NEAT1 over-expression, wherein the nucleotide sequence of said sgRNA is shown as SEQ ID NO: 1.

2. An adeno-associated virus AAV9-Neat1-sgRNA for long-chain non-coding RNA-NEAT1 over-expression, wherein said adeno-associated virus AAV9-Neat1-sgRNA comprises sgRNA; the nucleotide sequence of said sgRNA is shown as SEQ ID NO: 1.

3. The adeno-associated virus AAV9-Neat1-sgRNA according to claim 2, wherein the skeleton vector of said adeno-associated virus AAV9-Neat1-sgRNA comprises GV639 adenovirus vector.

4. The adeno-associated virus AAV9-Neat1-sgRNA according to claim 2, wherein the titer of the packaging of said adeno-associated virus AAV9-Neat1-sgRNA is $2 \times 10^{12}$ to $3 \times 10^{12}$ v.g./mL.

5. A method for treating Fuchs' endothelial corneal dystrophy, comprising administering to a subject in need thereof the adeno-associated virus AAV9-Neat1-sgRNA according to claim 2.

6. The method according to claim 5, wherein said adeno-associated virus AAV9-Neat1-sgRNA is administered by injecting into anterior chamber wherein an injection dosage of said adeno-associated virus AAV9-Neat1-sgRNA is 0.5 to 2 µL.

7. A pharmaceutical composition for relieving or treating Fuchs' endothelial cornea dystrophy, comprising the sgRNA according to claim 1.

8. A pharmaceutical composition for relieving or treating Fuchs' endothelial cornea dystrophy, comprising the adeno-associated virus AAV9-Neat1-sgRNA according to claim 2.

9. A pharmaceutical composition for relieving or treating symptoms of corneal edema or oxidative damage of corneal endothelium, comprising the sgRNA according to claim 1.

10. A method for treating symptoms of corneal edema or oxidative damage of corneal endothelium, comprising administering to a subject in need thereof the pharmaceutical composition of claim 9.

11. The pharmaceutical composition of claim 7, wherein the pharmaceutical composition is an injection.

12. The pharmaceutical composition according to claim 8, wherein the pharmaceutical composition is an injection.

13. The pharmaceutical composition according to claim 9, wherein the pharmaceutical composition is an injection.

\* \* \* \* \*

SEQUENCE LISTING

```
Sequence total quantity: 1
SEQ ID NO: 1            moltype = DNA  length = 21
FEATURE                 Location/Qualifiers
misc_feature            1..21
                        note = synthesized
source                  1..21
                        mol_type = other DNA
                        organism = synthetic construct
SEQUENCE: 1
aaggatcatt gagcaatctg a                                             21
```